United States Patent [19]

Bean et al.

[11] Patent Number: 5,470,711
[45] Date of Patent: Nov. 28, 1995

[54] SALIVA ENHANCEMENT REAGENT FOR FELINE LEUKEMIA VIRUS ELISA

[75] Inventors: Eric S. Bean, Escondido; Cheryl Waldman, San Diego; Ronald Sanders, Leucadia, all of Calif.

[73] Assignee: Synbiotics Corporation, San Diego, Calif.

[21] Appl. No.: 996,861

[22] Filed: Dec. 16, 1992

Related U.S. Application Data

[63] Continuation of Ser. No. 618,400, Nov. 27, 1990, abandoned, which is a continuation-in-part of Ser. No. 321,415, Mar. 17, 1988, abandoned, which is a continuation-in-part of Ser. No. 844,098, Mar. 26, 1986, Pat. No. 4,853,325.

[51] Int. Cl.⁶ .......................... G01N 33/53; G01N 33/569
[52] U.S. Cl. .......................... 435/7.1; 435/7.21; 435/7.72; 435/7.9; 435/7.92
[58] Field of Search ..................... 435/7.1, 7.21, 435/7.72, 7.9, 7.92; 436/4.1

[56] References Cited

U.S. PATENT DOCUMENTS

| | | | |
|---|---|---|---|
| 3,858,045 | 12/1974 | Waters | 435/35 |
| 4,663,277 | 5/1987 | Wang | 435/5 |
| 4,810,630 | 3/1989 | Craig et al. | 435/7 |
| 4,868,130 | 9/1989 | Hargreaves | 436/526 |

OTHER PUBLICATIONS

Francis et al. J. Clin. Pathol 32(5) 514–15 (1979).
Barrett, *Textbook of Immunology*, C. V. Mosby Co., 4th Ed., 1983, pp. 277–280.

Primary Examiner—W. Gary Jones
Assistant Examiner—Kenneth R. Horlick
Attorney, Agent, or Firm—Edward S. Irons

[57] ABSTRACT

A saliva enhancement reagent for use in an ELISA wherein a horseradish peroxidase (HRP) enzyme conjugate system is disclosed.

6 Claims, 1 Drawing Sheet

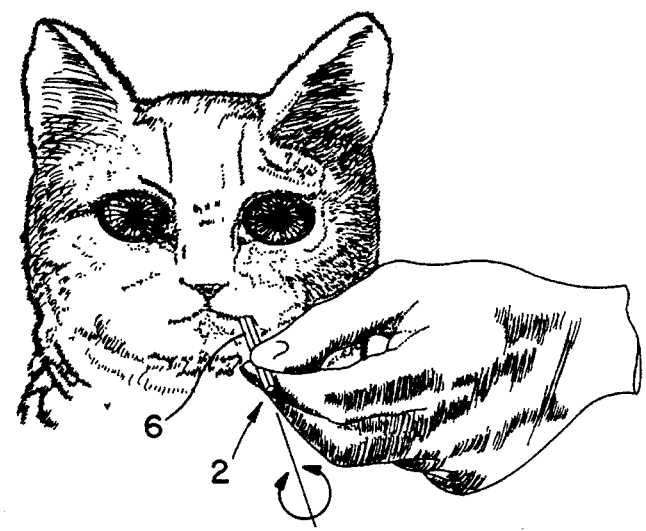
FIG. 1
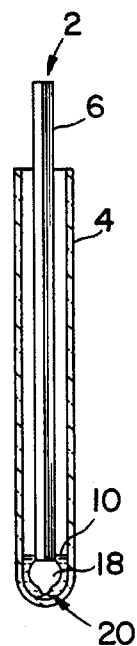
FIG. 2   FIG. 3
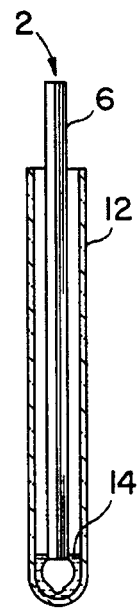
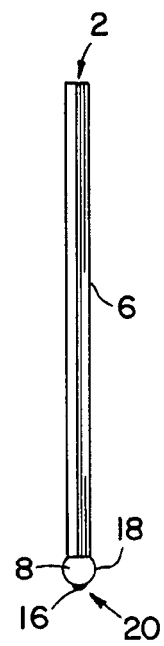
FIG. 4   FIG. 5
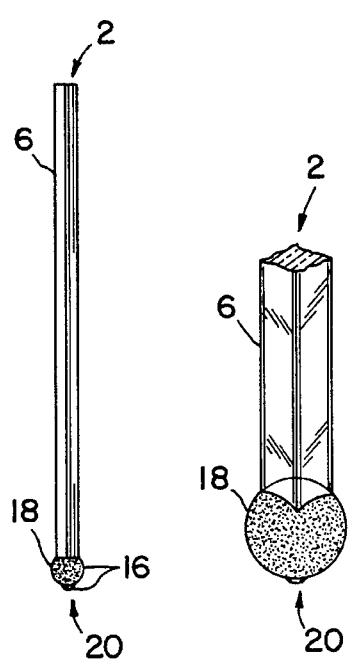
FIG. 6

SALIVA ENHANCEMENT REAGENT FOR FELINE LEUKEMIA VIRUS ELISA

This application is a continuation of application Ser. No. 618,400 filed Nov. 27, 1990, abandoned, continuation-in-part of application Ser. No. 321,415 filed March 17, 1988, abandoned which is a continuation-in-part of application Serial No. 844,098 filed Mar. 26, 1986 which issued as U.S. Pat. No. 4,853,325 on Aug. 1, 1989. The disclosure of application Serial No. 321,415 and of U.S. Pat. No. 4,853,325 are incorporated herein by reference.

TECHNICAL FIELD

This invention relates to an improved ELISA for the detection of FeLV group specific antigens in cat saliva. More particularly the invention relates to a saliva enhancement reagent for use in such an ELISA wherein a horseradish peroxidase (HRP) enzyme conjugate system is employed. The invention also relates to kits for detecting the presence of feline leukemia virus FeLV antigens in saliva samples.

BACKGROUND OF THE INVENTION

Pat. No. 4,853,325 describes a saliva test for FeLV. That test employs a probe having an immunochemically sensitive member for collecting saliva from the oral cavity of a cat and employs ELISA reagents for the incubation of the probe and the development of color reactions to indicate the presence or absence of FeLV within the saliva sample collected onto the probe.

The probe, wetted with cat saliva, is then incubated in an incubation vessel containing an enzyme conjugate of anti-FeLV antibodies in a solvent or diluent. Typical conjugate diluents include buffers such as phosphate, borate or carbonate; protein stabilizers such as bovine serum albumin (BSA), casein or gelatin; surfactants such as polyoxyethylene alcohols, polyoxyethylene fatty acid esters or alkylaryl polyether alcohols. The concentration of the conjugate in the diluent may lie from about 0.1 µg/mL (microgram per milliliter) to about 10.0 µg/mL. Unbound conjugate is removed. The bound conjugate which remains on the probe allows the immunologically sensitive member to be color developed. Color development indicates that FeLV and FeLV antigens were present in the saliva sample.

The specificity of this test is sometimes compromised by excessive nonspecific background and by false positives.

SUMMARY OF THE INVENTION

This invention provides a saliva enhancement reagent (SER) useful to reduce nonspecific background and false positives in saliva tests for FeLV of the type described in U.S. Pat. No. 4,853,325.

Pursuant to the invention the novel SER is added to the enzyme-antibody conjugate prior to use. It has been discovered that the presence in the conjugate diluent of an aqueous solution of saponin in a high salt buffer significantly reduces nonspecific background color in dipstick/saliva based assays which utilize HRP enzyme conjugate systems.

BRIEF DESCRIPTION OF THE FIGURES

FIG. 1 is a perspective view of a FeLV test probe inserted into a cat's oral cavity towards the buccal crease illustrating the process of rotating the probe.

FIG. 2 is a perspective view of the probe of FIG. 1 inserted into an incubation vessel illustrating the submersion of the immunochemically sensitive member of the probe within an incubation reagent. The nipple shaped control submember is shown to support the test submember slightly above the bottom of the incubation vessel, the shape of which minimizes the volume of incubation reagent required to surround the test submember.

FIG. 3 is a perspective view of the probe of FIG. 2 inserted into a development vessel and submerged in a chromogenic substrate.

FIG. 4 is a perspective view of the probe of FIG. 3 illustrating a negative color development on the test submember, indicating an absence of FeLV and/or FeLV antigens in the saliva sample, and a positive color development on the control submember, indicating that the incubation and development reagents are active.

FIG. 5 is a perspective view of the probe of FIG. 3 illustrating a positive color development on the test submember, indicating the presence of FeLV and/or FeLV antigens in the saliva sample, and a positive color development on the control submember.

FIG. 6 is an enlarged fragment of the probe of FIG. 5 illustrating the frosted texture of the immunochemically sensitive member with positive color development.

DETAILED DESCRIPTION OF THE INVENTION

U.S. Pat. No. 4,853,325, column 5, line 13 to column 8, line 2 describes a FeLV saliva ELISA test of the kind in which this invention is useful.

The SER of this invention is added to the enzyme, preferably HRP, conjugate solution in which the cat saliva bearing probe is incubated.

Typical enzyme conjugate solutions include from about 0.1 µg/mL to about 10.0 µg/mL of the conjugate in a diluent such as:

Phosphate Buffered Saline (0.01 M phosphate)

1% BSA 0.1% phenol (0.0106 M)

0.5% Tween 20 (polyoxyethylene 20 sorbitan monolaurate)

Phosphate Buffered Saline

6% BSA 0.1% phenol 0.5% Tween 20

0.1 mg/mL mouse IgG (mouse immunoglobulin)

The SER of this invention is added to the conjugate diluent. The preferred amount of the SER is from about 0.1% w/v to about 1% w/v in a conjugate diluent as above.

The SER is a solution of saponin in a buffered concentrated salt solution. The salt is preferably sodium chloride NaCl but may also be potassium chloride or other non-interfering salt. The SER is buffered, preferably with HEPES (hydroxy-ethyl piperazine ethane sulfonic acid) to a pH from about 7 to 8, preferably about 7.5. Other buffers may be used, e.g., phosphate, borate or carbonate.

A preferred SER composition contains 1M NaCl, 1% (v/v) saponin 10 MM Hepes and, if desired 0.2% (v/v) cosmocil CQ (preservative) in the solvent or diluent medium. Saponin concentrations in the ranges of 0.1–2% v/v and NaCl concentrations from about 0.5 M to about 2.0 M may be utilized.

The kits of the invention include an enzyme antibody conjugate diluent, i.e., the SER described herein. More specifically, the kits include a probe for acquiring the saliva sample, the probe comprising a handle and a member coated with immobilized FeLV, e.g., anti-p27 antibody, an incubation solution including an enzyme conjugate of the anti-FeLV antibody, an incubation vessel, a developing solution containing a chromogenic substrate for generation of color in the presence of the enzyme conjugate, the SER of this invention and a container sized to contain the probe, the incubation solution, the developing solution, the incubation vessel and the SER solution.

EXAMPLE 1

This comparative example reports the results of FeLV testing on FeLV negative cats. The test procedure entailed the use of a kit of the kind described generally in U.S. Pat. No. 4,853,325. In this procedure, the test reagents were added at 100 ul per tube of conjugate prior to dipstick addition. After sampling the cat saliva the sticks were added to the various conjugates and the assay proceeded according to the stated protocol. At the end of the assay the substrate reaction was quenched with sulfuric acid and the optical densities were measured at 450 nm.

| Additive | Avg Absorption A450 nm |
|---|---|
| None (control) | .075 |
| 10 mM Hepes Buffer | .066 |
| 1M NaCl/10 mM Hepes | .024 |
| 1% Saponin/10 mM Hepes | .025 |
| 1M NaCl/1% Saponin/10 mM Hepes | .014 |

As shown above, the presence of Saponin or high salt decreases nonspecific background from the buffer control. Together the reagents reduce background by another two fold to 4.75 times less than the buffer control.

EXAMPLE 2

A group of FeLV negative cats were subjected to a saliva test for FeLV. In each case the test was carried out using a kit of the kind generally described in U.S. Pat. No. 4,853,325.

The results of these tests are set forth in Table I.

TABLE I

| | Abs 450 nm | | | | |
|---|---|---|---|---|---|
| CAT ID# | SER | control | CAT ID# | SER | control |
| 36453 | 0.014 | 0.028 | 36830b | 0.015 | 0.045 |
| 36423a | 0.013 | 0.025 | 36830c | 0.019 | 0.046 |
| 36423b | 0.007 | 0.022 | 281148f | 0.022 | 0.04 |
| 36423c | 0.01 | 0.063 | 281148g | 0.013 | 0.023 |
| 36296 | 0.033 | 0.03 | 281148h | 0.009 | 0.017 |
| 36340a | 0.017 | 0.044 | 36825 | 0.008 | 0.029 |
| 36340b | 0.004 | 0.031 | 36825a | 0.026 | 0.025 |
| 36340c | 0.008 | 0.037 | 36825b | 0.012 | 0.037 |
| 36365 | 0.008 | 0.024 | 36816 | 0.016 | 0.023 |
| 36386 | 0.01 | 0.046 | 281148i | 0.009 | 0.034 |
| 36222 | 0.006 | 0.028 | 281148j | 0.016 | 0.027 |
| 36343 | 0.022 | 0.087 | 36827a | 0.031 | 0.023 |
| 36188 | 0.006 | 0.081 | 36827b | 0.01 | 0.015 |
| 36364 | 0.005 | 0.042 | 36827c | 0.015 | 0.026 |
| 36217 | 0.005 | 0.053 | 36827d | 0.01 | 0.019 |
| 36346a | 0.01 | 0.042 | 281148k | 0.013 | 0.059 |
| 36346b | 0.01 | 0.05 | 80413 | 0.01 | 0.031 |
| 36346c | 0.007 | 0.039 | 76022 | 0.012 | 0.026 |
| 36417a | 0.009 | 0.049 | 76021 | 0.005 | 0.027 |
| 36417b | 0.003 | 0.035 | 76036 | 0.007 | 0.048 |
| 36417c | 0.013 | 0.07 | 80830 | 0.007 | 0.04 |
| 36191 | 0.011 | 0.047 | 80405 | 0.021 | 0.089 |
| 36264 | 0.008 | 0.034 | 80832 | 0.021 | 0.079 |
| 36418 | 0.014 | 0.035 | 76037 | 0.011 | 0.058 |
| 36416 | 0.022 | 0.059 | 76038 | 0.01 | 0.029 |
| 36366 | 0.008 | 0.052 | 80428a | 0.011 | 0.026 |
| 36812a | 0.027 | 0.032 | 80428b | 0.015 | 0.043 |
| 36812b | 0.007 | 0.047 | 80428c | 0.009 | 0.032 |
| 281148a | 0.01 | 0.034 | 36946 | 0.012 | 0.084 |
| 281148b | 0.024 | 0.03 | 36936 | 0.027 | 0.022 |
| 281148c | 0.016 | 0.045 | 76027a | 0.012 | 0.048 |
| 281148d | 0.009 | 0.032 | 76027b | 0.026 | 0.035 |
| 281148e | 0.023 | 0.05 | 76051a | 0.01 | 0.034 |
| 366151 | 0.011 | 0.026 | 76051b | 0.012 | 0.051 |
| 36830a | 0.01 | 0.042 | | | |

| | SER | control |
|---|---|---|
| Mean | 0.013 | 0.04 |
| Std Dev | 0.006 | 0.017 |

All of these cats are FeLV negative. Table I shows that the signal obtained with the SER is approximately 30% of that obtained with the standard formulation.

EXAMPLE 3

This example reports the result of a clinical evaluation of the SER of this invention.

FeLV infected cats were tested, in each case, in the manner described in Example 2.

The results of this clinical evaluation are set forth in Table II.

TABLE II

| | | SER | | control | |
|---|---|---|---|---|---|
| # | Cat Identification | Visual | A450 | Vis. | A450 |
| 1 | Whitey | + | .238 | + | .578 |
| 2 | Spazz | + | .214 | + | .745 |
| 3 | Midnight | + | .460 | + | .634 |
| 4 | Nave | + | .564 | + | .604 |
| 5 | Smudge | + | .478 | + | .466 |
| 6 | Marble | + | .100 | + | .265 |
| 7 | Pazuzu | + | .461 | + | .471 |
| 8 | Winky | + | .444 | + | .706 |
| 9 | Drop Off | + | .400 | + | .462 |
| 10 | Easter | + | .289 | + | .648 |
| 11 | Slots | + | .140 | + | .393 |
| 12 | Blackjack | + | .167 | + | .276 |
| 13 | Roulette | + | .467 | + | .729 |
| 14 | Bingo | + | .397 | + | .616 |
| 15 | Vegas | + | .695 | + | .863 |
| 16 | Lovely Rita | + | .402 | + | .572 |
| 17 | Barbie | + | .117 | + | .620 |
| 18 | Rhoda | + | .428 | + | .773 |
| 19 | Samba | + | .177 | + | .434 |
| 20 | Tomascena | + | .132 | + | .273 |
| 21 | Petite Pearl | − | .012 | − | .041 |
| 22 | Sveetie | − | .012 | − | .058 |
| 23 | Josie | − | .015 | − | .049 |
| 24 | Blackstone | − | .014 | − | .045 |

Cats 21–24 had tested positive for FeLV in the past, but the disease is latent in these animals, and they were not shedding virus at the time of the test. They are currently negative in both formats. All other FeLV positive cats yielded positive test results in both formats.

Positive results are those samples which are distinctly blue after the substrate incubation times. This correlates to A450>.075. A direct comparison of Absorbances between the two test formats is difficult because of antigen sampling variation inherent in the saliva assay. This is deemed largely irrelevant due to the qualitative nature of the test.

We claim:

1. A method for detecting feline leukemia virus comprising obtaining a saliva sample from a cat with a dipstick and subjecting said sample to an ELISA assay involving anti-FeLV antibodies and an enzyme-antibody conjugate, wherein the improvement consists essentially of adding a saliva enhancement reagent to said conjugate prior to use in said method such that non-specific background color formation in said method is reduced, wherein said saliva enhancement reagent consists essentially of an aqueous solution containing from about 0.1% to about 2.0% by weight saponin and being from about 0.5 to about 2.0 molar in sodium chloride, said solution being buffered to a pH of from about 7.0 to about 8.0.

2. The method of claim 1, wherein said aqueous solution comprises 1 M sodium chloride 1% saponin/10 mM HEPES.

3. A method for determining whether a cat has persistent, feline leukemia virus induced viremia, comprising obtaining a saliva sample from a cat and subjecting said sample to an ELISA assay involving anti feline leukemia virus antibodies and in which the enzyme conjugate is a horseradish peroxidase conjugate, wherein the improvement comprises utilizing as a diluent for said conjugate an aqueous solution comprising saponin and sodium chloride, said solution being buffered to a pH of from about 7.0 to about 8.0 and containing from about 0.1% to about 2.0% by weight saponin and being from about 0.5 to about 2.0 molar in sodium chloride.

4. The method of claim 3, wherein said solution is buffered with HEPES.

5. A method for detecting feline leukemia virus (FeLV), comprising obtaining a saliva sample from a cat with a dipstick and subjecting said sample to an ELISA assay involving anti-FeLV antibodies and in which the enzyme conjugate is a horseradish peroxidase conjugate, wherein the improvement comprises utilizing as a diluent for said conjugate a buffered aqueuos solution of saponin wherein nonspecific background color is reduced.

6. A kit for acquiring a saliva sample from the oral cavity of a cat and for detecting feline leukemia virus (FeLV) infection in said cat, comprising:

a probe for acquiring the saliva sample, said probe comprising a handle connected to an immunochemically sensitive member having a test member coated with immobilized anti-p27 antibody, to allow insertion of said member into the oral cavity of a cat and manipulation of said member for acquiring a saliva sample, an incubation solution including a soluble enzyme conjugate of an anti-p27 antibody, an incubation vessel shaped to contain said incubation solution and to closely fit around said immunochemically sensitive member of said probe, a developing solution containing a chromogenic substrate capable of generating color in the presence of said soluble enzyme conjugate, a conjugate diluent solution as defined in claim 3 or claim 4, and a container sized to contain said probe, said incubation solution, said developing solution, and said incubation vessel

* * * * *